(12) United States Patent
Komatsu

(10) Patent No.: US 6,913,663 B2
(45) Date of Patent: Jul. 5, 2005

(54) METHOD FOR FABRICATING A MAGNETIC THERAPEUTIC DEVICE

(75) Inventor: Katsumi Komatsu, Osaka (JP)

(73) Assignee: Arc Quest Co., Ltd., Osaka (JP)

( * ) Notice: Subject to any disclaimer, the term of this patent is extended or adjusted under 35 U.S.C. 154(b) by 232 days.

(21) Appl. No.: 10/256,332

(22) Filed: Sep. 26, 2002

(65) Prior Publication Data

US 2004/0060651 A1 Apr. 1, 2004

(51) Int. Cl.[7] .............................................. A61N 2/06
(52) U.S. Cl. ........................................ 156/60; 600/15
(58) Field of Search ............................ 156/60; 2/115, 2/311; 60/9, 15; 335/302, 303, 306

(56) References Cited

U.S. PATENT DOCUMENTS

| | | | | |
|---|---|---|---|---|
| 5,707,333 A | * | 1/1998 | Bakst | ........................... 600/9 |
| 5,950,239 A | * | 9/1999 | Lopez | ........................... 2/115 |
| 6,328,684 B1 | * | 12/2001 | Ardizzone | ..................... 600/9 |
| 6,551,234 B1 | * | 4/2003 | Martello | ...................... 600/15 |
| 6,652,446 B1 | * | 11/2003 | Bove et al. | ................... 600/15 |

* cited by examiner

*Primary Examiner*—John T. Haran
(74) *Attorney, Agent, or Firm*—Smith, Gambrell & Russell, LLP

(57) ABSTRACT

A dummy member is covered with a sheet member in a manner to keep one side of the sheet member in contact with the dummy member retaining a plurality of permanent magnets in a manner that any pair of adjoining magnets are opposite in polarity. A plurality of permanent magnets are supplied to the other side of the sheet member conforming to the dummy member so as to be magnetically attracted by the permanent magnets of the dummy member whereby the therapeutic permanent magnets are positioned at predetermined places on the other side of the sheet member. Subsequently, the therapeutic permanent magnets arranged on the other side of the sheet member are fixed to the sheet member.

4 Claims, 5 Drawing Sheets

METHOD FOR FABRICATING A MAGNETIC THERAPEUTIC DEVICE

BACKGROUND OF THE INVENTION

The present invention relates to a method for fabricating a magnetic therapeutic device to be fitted on the body or some part thereof for treating shoulder stiffness, low back pain or the like.

OBJECT OF THE INVENTION

Heretofore, there have been provided various magnetic therapeutic devices for treating shoulder stiffness, which include an undergarment, such as formed like a tank top or the like, having permanent magnets attached thereto; a wide belt having permanent magnets attached thereto and designed to be wrapped around the waist; and the like. The magnetic therapeutic devices are arranged such that the undergarment or belt has a plurality of permanent magnets attached to place in correspondence to an area of the body that produces pain sensations. As fitted on the body or some part thereof, the magnetic therapeutic device is adapted to treat the shoulder stiffness or low back pain by applying a magnetic energy of the permanent magnets for increasing blood circulation or relaxing muscle.

For achieving an enhanced therapeutic effect, the magnetic therapeutic device of this type may preferably employ anisotropic magnets as the permanent magnets which are arranged in a manner that any pair of adjoining magnets exhibit opposite polarities at their sides facing the body surface. The reason is because magnetic flux lines emanating from, for example, the north pole of one permanent magnet reach not only the south pole thereof but also the south poles of the adjoining permanent magnets so that the magnetic energy penetrates deep into a wide area of the body.

However, many of the conventional magnetic therapeutic devices have an arrangement wherein all the permanent magnets exhibit the same polarity at their sides facing the body surface. This results from a method of fabricating the magnetic therapeutic devices. Specifically, the conventional magnetic therapeutic device is fabricated in a manner that discs such as formed of an iron-based metal as a material for the permanent magnets are attached to predetermined places of the undergarment or belt and then all the discs are magnetized at a time so as to obtain the permanent magnets. Thus, all the permanent magnets naturally exhibit the same polarity at their sides facing the body surface. Although such a fabrication method has an advantage of efficiently producing the magnetic therapeutic devices at low costs, the resultant magnetic therapeutic devices have a low therapeutic effect on the shoulder stiffness and the like.

In the magnetic therapeutic device wherein any pair of adjoining permanent magnets present the opposite polarities at their sides facing the body surface, on the other hand, each of the previously prepared permanent magnets must be attached to each place on the undergarment or belt after the polarity thereof is identified. This leads to a drawback of low production efficiency and high production costs.

Therefore, it is an object of the invention to provide an efficient fabrication method for magnetic therapeutic device wherein any pair of adjoining permanent magnets present the opposite polarities at their sides facing the body surface.

SUMMARY OF THE INVENTION

A method for fabricating a magnetic therapeutic device according to the invention comprises the steps of: covering a dummy member with a sheet member in a manner to keep one side of the sheet member in contact with the dummy member retaining a plurality of permanent magnets in a manner that any pair of adjoining permanent magnets are opposite in polarity; supplying a plurality of permanent magnets to the other side of the sheet member conforming to the dummy member while permitting the permanent magnets of the dummy member to magnetically attract the supplied magnets, thereby arranging the therapeutic permanent magnets at predetermined places on the other side of the sheet member; and fixing the therapeutic permanent magnets to the sheet member, the magnets arranged on the other side of the sheet member.

According to such a method for fabricating the magnetic therapeutic device, the therapeutic permanent magnets are simply supplied to the other side of the sheet member, the one side of which conforms the dummy member, whereby the therapeutic permanent magnets are quickly placed at predetermined positions on the sheet member as magnetically attracted by the permanent magnets in the dummy member. On the other hand, the dummy member retains the permanent magnets in a manner that any pair of adjoining magnets are opposite in polarity and hence, the therapeutic permanent magnets are arranged on the sheet member in a similar manner that any pair of adjoining magnets are opposite in polarity. This negates the need for identifying the polarity of each permanent magnet before attaching it to the sheet member. Accordingly, there is accomplished an efficient, low-cost fabrication of the magnetic therapeutic device wherein any pair of adjoining permanent magnets exhibit opposite polarities at their sides facing the body surface.

It is preferred to employ the dummy member wherein the permanent magnets are embedded in retaining members, respectively. In this case, the permanent magnets are prevented from projecting from a surface of the dummy member, which permits the sheet member to conform to the dummy member in an easy and positive manner.

According to the above method for fabricating the magnetic therapeutic device, the sheet member may be a fabric forming a tank top. In this case, a tank-top type magnetic therapeutic device may be efficiently fabricated at low costs. It is preferred in this case that a dressmaker's model shaped like a human body is used as the dummy member, and that the therapeutic permanent magnets are supplied to the tank top fitted on the dressmaker's model. This ensures that the permanent magnets are placed at correct positions on the fabric.

DETAILED DESCRIPTION OF THE PREFERRED EMBODIMENT

The invention will hereinbelow be described in detail with reference to the accompanying drawings illustrating the preferred embodiments hereof.

Figure 1:
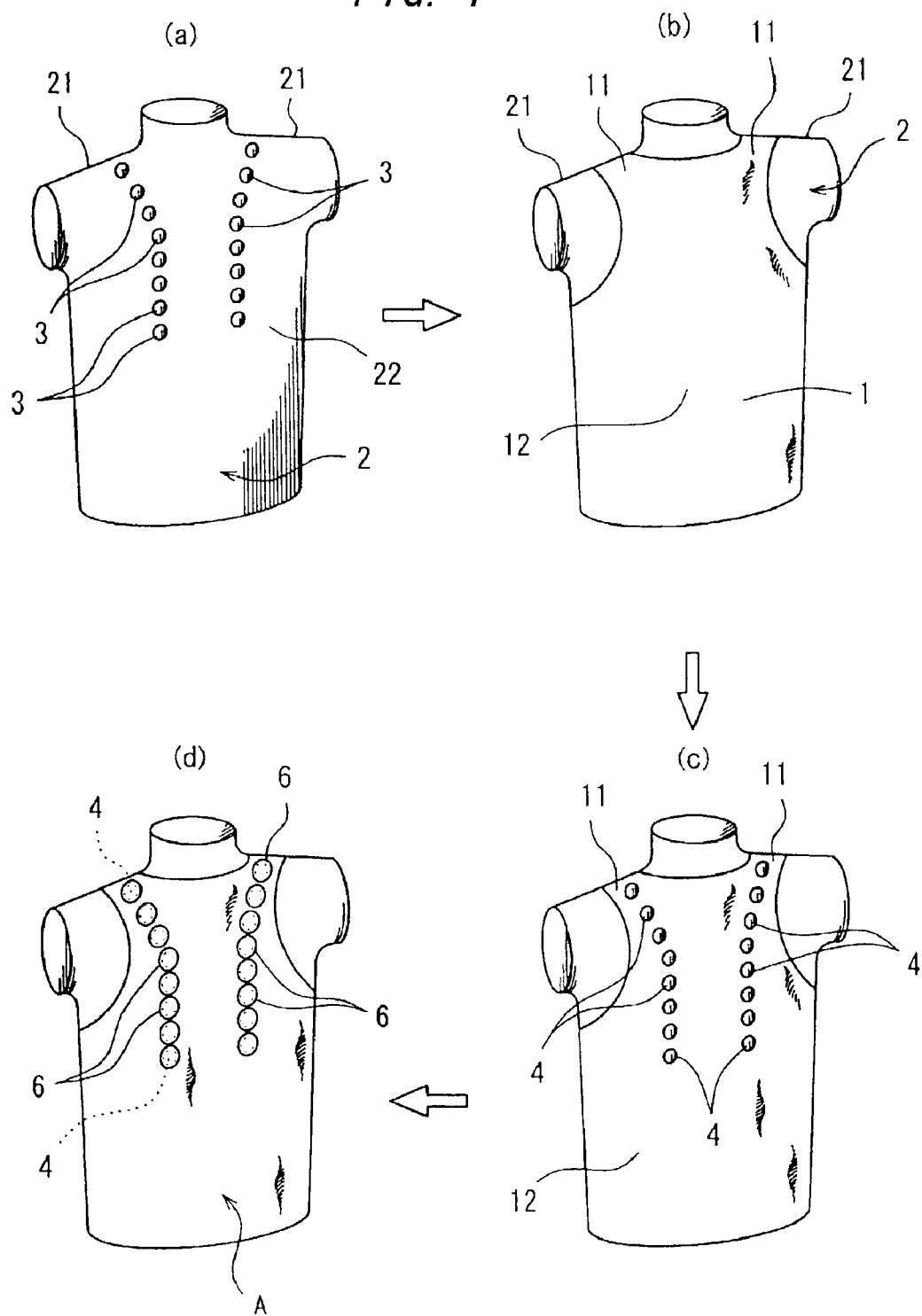
FIG. 1 is a group of diagrams showing the steps of fabricating a magnetic therapeutic device according to one embodiment of the invention.

FIG. 1 is a group of diagrams showing the steps of fabricating a magnetic therapeutic device according to the invention. The embodiment shown in FIG. 1 illustrates the steps of fabricating a tank-top type magnetic therapeutic device.

Firstly, as shown in (a) and (b) in FIG. 1, a previously prepared tank top 1 for magnetic therapeutic device is fitted on a dummy member 2. At this time, the tank top 1 is turned inside out before fitted on the dummy member 2. This brings a front side of the tank top 1 fabric into contact with the dummy member 2.

Figure 2:
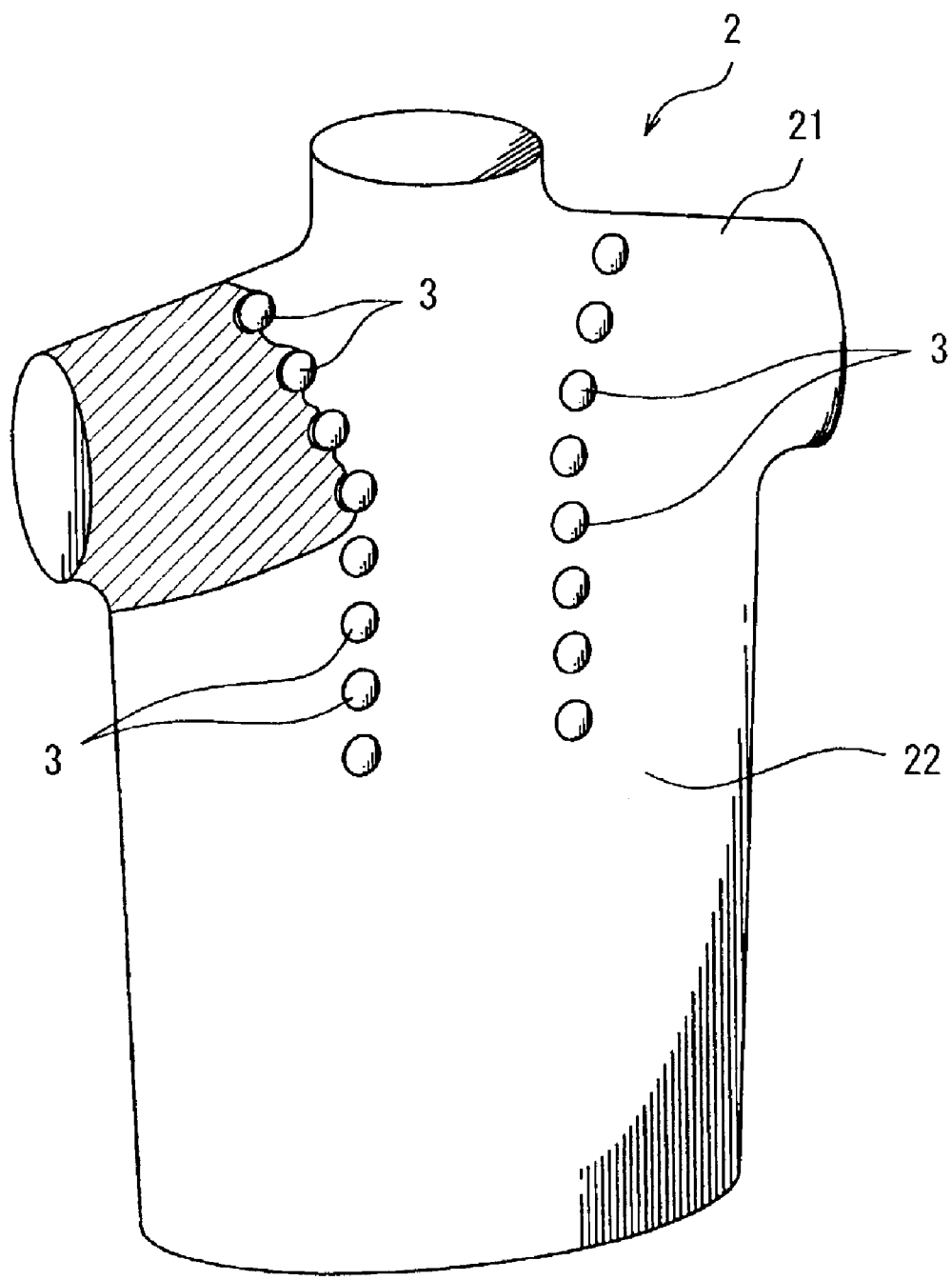
FIG. 2 is a partially cut-away perspective view showing a dummy member.
Figure 3:
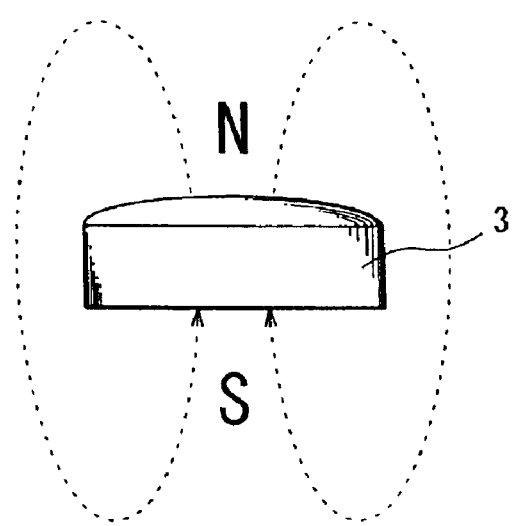
FIG. 3 is a side view of a permanent magnet.
Figure 4:
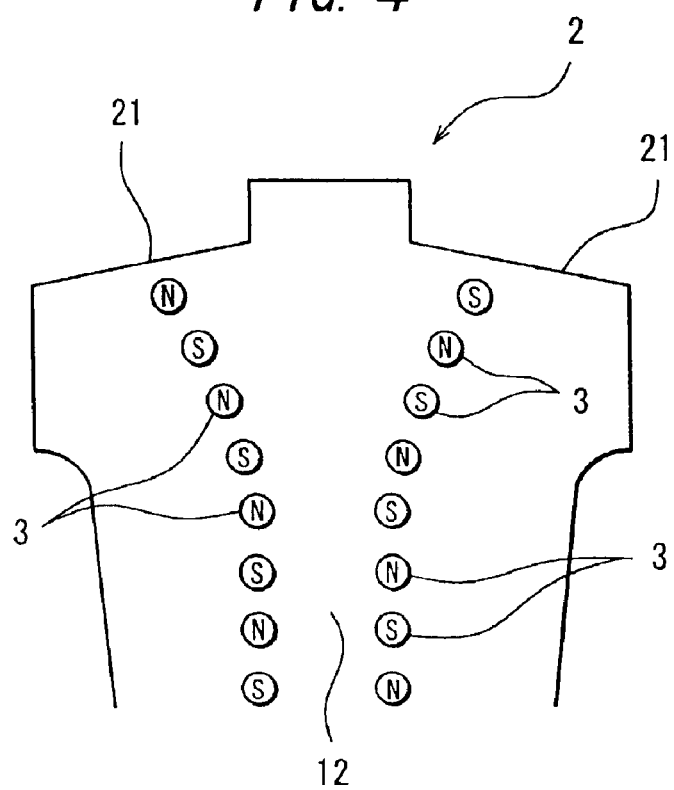
FIG. 4 is a schematic diagram showing an arrangement of the permanent magnets.

The dummy member 2 is composed of a dressmaker's model shaped like a human body, having a plurality of disc-like permanent magnets 3 embedded in each of shoulder portions 21 and back portions 22 thereof. The permanent magnet 3 is an anisotropic ferrite magnet having the south pole on one side thereof and the north pole on the other side thereof (see FIG. 3). The permanent magnets 3 are arranged in a line extended from the shoulder portion 21 to the back portion 22 on each of the opposites sides of the body. The permanent magnets 3 on the shoulder portions 21 and the back portions 22 are positioned at individual places at least corresponding to trapezius muscles extending from the shoulders to the back. The permanent magnets 3 on the back portions 22, in particular, are positioned in correspondence to pressure points or pressure point areas on opposite sides of the spine. Any pair of vertically or laterally adjoining permanent magnets 3 are arranged in oppositely oriented relation so that any magnet may be opposite in polarity to the individual neighboring magnets (see FIG. 4). Furthermore, the permanent magnets 3 are so embedded in the dummy member 2 as to be flush with a surface of the dummy member 2 (see FIG. 2). Therefore, the surface of the dummy member 2 is free from projections defined by the permanent magnets 3, so that the tank top 1 can conform to the dummy member 2 easily and precisely.

Figure 5:
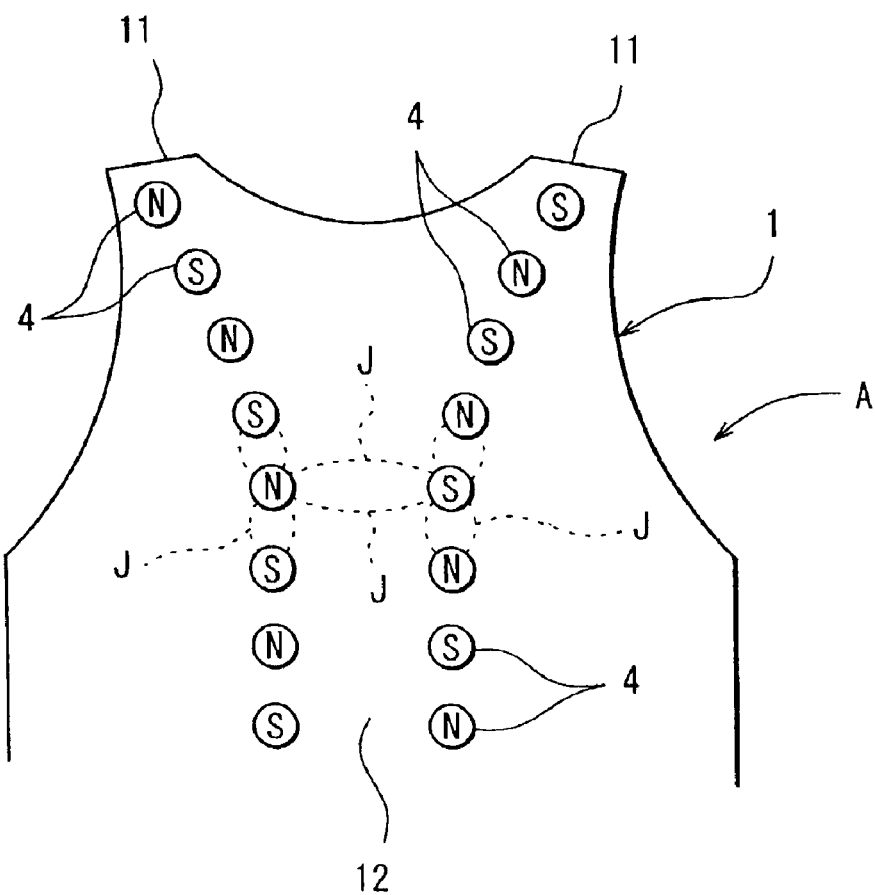
FIG. 5 is a schematic diagram showing an arrangement of magnets on a magnetic therapeutic device.

Next, a plurality of therapeutic permanent magnets 4 are supplied to areas including shoulder portions 11 and back portions 12 of the tank top 1 fitted on the dummy member 2 so as to be magnetically attracted by the permanent magnets 3 of the dummy member 2 (see (c) in FIG. 1). This permits the therapeutic permanent magnets 4 to be arranged on the tank top 1 in correspondence to a layout pattern of the permanent magnets 3 of the dummy member 2. Since the respective permanent magnets 3 embedded in the dummy member 2 are opposite in polarity to the individual neighboring magnets 3, the respective therapeutic permanent magnets 4 on the tank top 1 may have the opposite polarity to that of the individual neighboring magnets 4 (see FIG. 5). This negates the need for identifying the polarity of each therapeutic permanent magnet 4 before attaching it to the tank top 1. In addition, the permanent magnets 3 of the dummy member 2 ensures that the therapeutic permanent magnets 4 are precisely placed at proper positions on the tank top 1. Incidentally, remaining permanent magnets 4, allowed to fall as not being attracted by the permanent magnets 3 of the dummy member 2, are collected to be used as the permanent magnets 4 for another tank top 1.

Subsequently, the therapeutic permanent magnets 4 arranged on the tank top 1 are fixed thereto (see (d) in FIG. 1). A preferred method for fixing the magnets includes the steps of: overlaying a circular sheet 6 on the therapeutic permanent magnet 4, the sheet applied with a hot-melt adhesive on one side thereof; and heating a peripheral portion of the circular sheet 6 over the magnet 4 by means of a heating device thereby fusing the adhesive. In this manner, the tank-top type magnetic therapeutic device A is fabricated wherein the therapeutic permanent magnets 4 are fixed to places of the shoulder portions 11 and back portions 12.

The magnetic therapeutic device A thus fabricated is adapted to bring the therapeutic permanent magnets 4 into correspondence to the pressure points or the pressure point areas on the opposite sides of the spine and hence, is capable of effectively stimulating the pressure points by way of the magnetic energy of the magnets. Thus is provided an effective therapy of the shoulder stiffness.

Furthermore, the device employs the anisotropic magnets as the permanent magnets 4 which are arranged in a manner that any pair of adjoining magnets are opposite in polarity at their sides facing the body surface. Therefore, the magnetic flux lines J emanating from the north pole of one permanent magnet 4 reach not only the south pole thereof but also the south poles of the adjoining permanent magnets 4 (see FIG. 5). This permits the magnetic energy to penetrate deep into a wide area of the body, contributing to an even more effective therapy of the shoulder stiffness.

Figure 6:
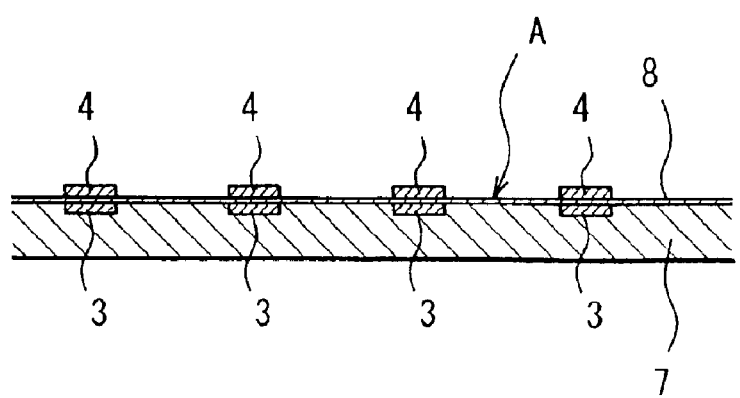
FIG. 6 is a sectional view showing another embodiment of the invention.
Figure 7:
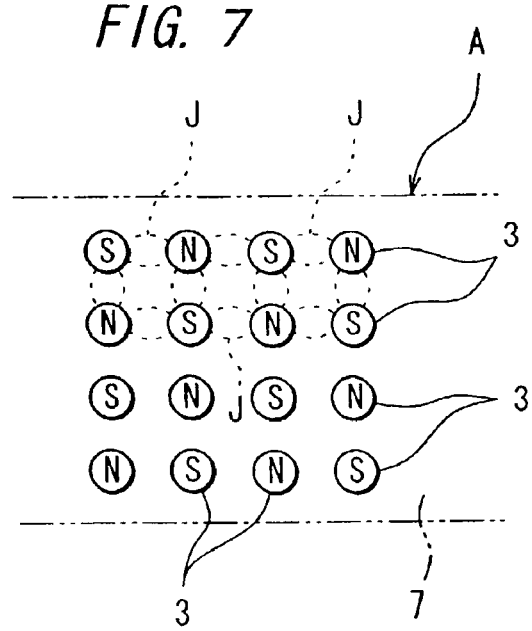
FIG. 7 is a schematic diagram showing an arrangement of the permanent magnets.

The dummy member 2 may take any of various shapes according to the shape of the magnetic therapeutic device A. In the case of a dummy member 2 for use in the fabrication of a belt-type magnetic therapeutic device A to be wrapped around the waist, for example, there may be used a dummy member 2 wherein a plurality of permanent magnets 3 are embedded in a flat plate 7 (see FIG. 6). In this case, as well, the permanent magnets 3 are arranged such that any pair of adjoining permanent magnets 3 are opposite in polarity (see FIG. 7). The belt-type magnetic therapeutic device A is fabricated as follows. A piece fabric for belt (sheet member) 8 is overlaid on the dummy member 2 in a manner to keep one side of the fabric in contact with the dummy member while the therapeutic permanent magnets 4 are supplied to the other side of the fabric. Thus, the therapeutic permanent magnets 4 are arranged on the fabric.

Figure 8:
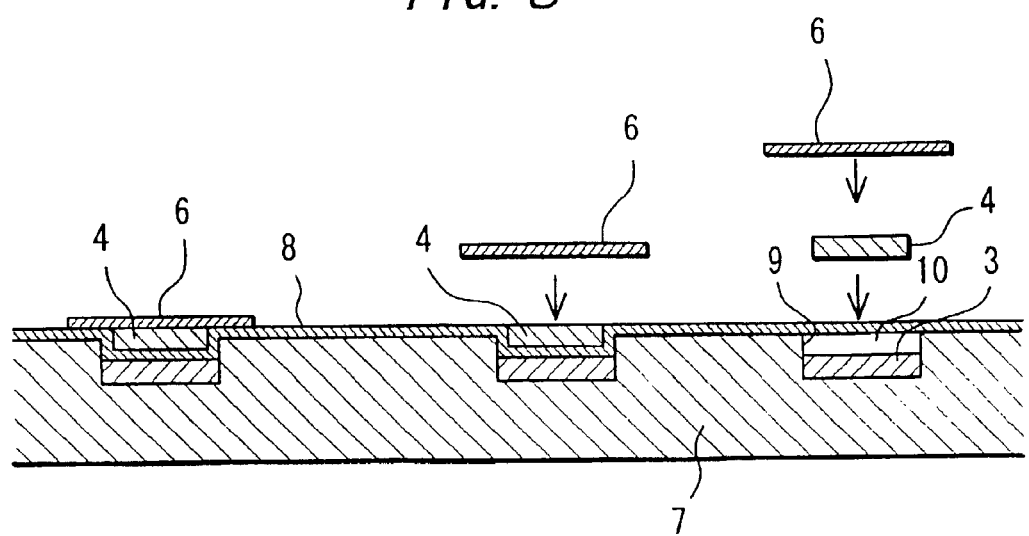
FIG. 8 is a sectional view showing still another embodiment of the invention.

FIG. 8 is a sectional view showing another embodiment of the invention. In this embodiment, the dummy member 2 is formed with deep holes 9, each of which holds the permanent magnet 3 on its bottom and includes a cavity 10 defined between a top surface of the dummy member 2 and a top surface of the permanent magnet 3. The cavity has a depth equal to the thickness of the therapeutic permanent magnet 4. In this case, the therapeutic permanent magnets 4 arranged on the fabric 8 are pressed in the cavities 10 along with the fabric 8, whereby top surfaces of the therapeutic permanent magnets 4 become substantially flush with the surface of the dummy member 2. Accordingly, the circular sheets 6 may be received by both the fabric 8 and the dummy member 2 when the therapeutic permanent magnets 4 are fixed to the fabric 8. Thus, the circular sheets 6 can be readily affixed to the fabric 8.

What is claimed is:

1. A method for fabricating a magnetic therapeutic device comprising the steps of:

providing a dummy member retaining a plurality of permanent magnets in a manner that any pair of adjacent permanent magnets are opposite in polarity;

covering the dummy member with a sheet member in a manner to keep one side of the sheet member in contact with the dummy member;

supplying a plurality of therapeutic permanent magnets to the other side of the sheet member conforming to the dummy member while permitting the permanent magnets of the dummy member to magnetically attract the supplied therapeutic permanent magnets, thereby arranging the therapeutic permanent magnets at predetermined places on the other side of the sheet member such that adjacent therapeutic permanent magnets are opposite in polarity; and fixing the therapeutic permanent magnets to the other side of the sheet member.

2. A method for fabricating the magnetic therapeutic device as claimed in claim 1, wherein the permanent magnets are embedded in the dummy member.

3. A method for fabricating the magnetic therapeutic device as claimed in claim 1, wherein the sheet member is a fabric forming a tank top.

4. A method for fabricating the magnetic therapeutic device as claimed in claim 3, wherein a dressmaker's model shaped like a human body is used as the dummy member, and wherein the therapeutic permanent magnets are supplied to the tank top fitted on the dressmaker's model.

* * * * *